US012012551B2

(12) United States Patent
McIntosh (10) Patent No.: US 12,012,551 B2
(45) Date of Patent: *Jun. 18, 2024

(54) SYSTEMS AND METHODS OF USE OF UV-RESPONSIVE LAMINATES AND METHODS OF FABRICATION THEREOF

(71) Applicant: THE BOEING COMPANY, Chicago, IL (US)

(72) Inventor: Darren C. McIntosh, Mukilteo, WA (US)

(73) Assignee: THE BOEING COMPANY, Arlington, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/484,987

(22) Filed: Sep. 24, 2021

(65) Prior Publication Data

US 2022/0177776 A1    Jun. 9, 2022

Related U.S. Application Data

(60) Provisional application No. 63/121,476, filed on Dec. 4, 2020.

(51) Int. Cl.
*C09K 9/00* (2006.01)
*B08B 7/00* (2006.01)

(52) U.S. Cl.
CPC ............. *C09K 9/00* (2013.01); *B08B 7/0057* (2013.01)

(58) Field of Classification Search
CPC . C09K 9/00; B08B 7/0057; A61L 2/00; A61L 2/08; A61L 2/10; A61L 2/28
See application file for complete search history.

(56) References Cited

U.S. PATENT DOCUMENTS 3,899,188 A    8/1975    Curry
4,418,508 A    12/1983   Gilliland et al.
(Continued)

FOREIGN PATENT DOCUMENTS

CN    1076902 A    10/1993
CN    201881925 U    6/2011
(Continued)

OTHER PUBLICATIONS

Machine Translation of WO89/11714, Ochi et al.; Laminar Structure Capable of Generating Information Upon Irradiation With Ultraviolet Rays (Year: 1989).*
(Continued)

*Primary Examiner* — Sharidan Carrillo
(74) *Attorney, Agent, or Firm* — Patterson + Sheridan, LLP (57) ABSTRACT

The present disclosure provides for UV-responsive laminates including a first layer having a photochromatic pigment arranged as a pigment texture, or one or more photochromatic indicators, or combinations thereof. The photochromatic pigment may be disposed on the laminate during laminate fabrication, prior to installation of the laminate, or in-situ, subsequent to installation. The photochromatic pigment is configured to change from a first state to a second state in response to exposure to an ultraviolet (UV) light source, the first state is invisible to a naked eye under ambient lighting and the second state is visible to the naked eye under ambient lighting. The UV-responsive laminates may further include additional layers, such as a second layer which may be a coupling layer configured to removably couple the laminate to a component. Additional layers, such as a protective layer or a backing layer, may be included in the UV-responsive laminate as well.

20 Claims, 7 Drawing Sheets

(56) References Cited

U.S. PATENT DOCUMENTS

| | | | |
|---|---|---|---|
| 5,581,090 | A | 12/1996 | Goudjil |
| 6,475,433 | B2 | 11/2002 | McGeorge et al. |
| 10,112,378 | B2 | 10/2018 | Barboza |
| 10,512,704 | B2 | 12/2019 | Dytioco et al. |
| 2001/0048891 | A1 | 12/2001 | McGeorge et al. |
| 2003/0031586 | A1 | 2/2003 | Eckhardt et al. |
| 2015/0343102 | A1* | 12/2015 | Romo ................ A61L 2/10 436/1 |
| 2017/0080747 | A1 | 3/2017 | Young et al. |
| 2017/0157279 | A1* | 6/2017 | Dayton ............... G03C 1/733 |
| 2018/0369440 | A1 | 12/2018 | Dytioco et al. |
| 2019/0351086 | A1 | 11/2019 | Dayton |
| 2022/0096680 | A1* | 3/2022 | McIntosh ............ A61L 2/28 |
| 2022/0177776 | A1* | 6/2022 | McIntosh ............ G01J 1/429 |

FOREIGN PATENT DOCUMENTS

| | | | | |
|---|---|---|---|---|
| CN | 102239087 | A | 11/2011 | |
| CN | 202243127 | U | 5/2012 | |
| CN | 105300709 | A | 2/2016 | |
| EP | 3000593 | A1 * | 3/2016 | ............ B32B 27/08 |
| EP | 3061601 | A1 * | 8/2016 | ............ B32B 15/08 |
| KR | 20060127828 | A | 12/2006 | |
| WO | 8911714 | A1 | 11/1989 | |
| WO | WO-2010128063 | A2 * | 11/2010 | ............ C09B 19/02 |
| WO | 2015042169 | A1 | 3/2015 | |
| WO | WO-2015184190 | A1 * | 12/2015 | ............... A61L 2/00 |

OTHER PUBLICATIONS

NIGK Corporation, "Color changing adhesive UV monitor label/Single use/Color changing sticker," Dated Nov. 28, 2020, pp. 1-4, <https://web.archive.org/web/20201128220417/https://www.nichigi.co.jp/blog/uvlabel/20200715_saitamashimbun>.

QuantaDose, "1st Edition, NeX-Gen Rapid UVGI Detection," QuantaDose™, (Year: 2020), Dated Sep. 28, 2020, <https://web.archive.org/web/20200928042202/https://www.quantadose.com/quantadose-1st-edition-uvc-test-card-vs-quantadose-2nd-edition-uvc-test-card-vs-uvc-light-installer-package/>.

Shannon McMahon, "Plane cabins could change dramatically because of the pandemic. Here's how," The Washington Post, Dated Aug. 18, 2020, pp. 1-10.

Hallcrest, "Temperatire Data Loggers & Indicators for Wireless Monitoring: Temperature Monitoring," SpotSee, Dated Aug. 17, 2020, <https://www.hallcrest.com/DesktopModules/Bring2mind/DMX/Download.aspx?EntryId=274>.

Suzanne Latta, "UV Irreversible Indicator," Healthmark Industries Co., dated Aug. 5, 2020, pp. 1-2.

Unkown, "Santinelli International Optical Supplies," Date: Aug. 17, 2020, pp. 1-3 <https://siosopticalppe.com/product/uv-dose-indicator-cards-for-uv-fusion/>.

Unkown, "American Ultraviolet—Dosimeter," Ameircan Ultraviolet, Date Accessed: Aug. 12, 2020, pp. 1-4 <https://store.auvhealthcare.com/>.

Augusta Statz, "THese New UV-Activated Sneakers From Converse Change From White to a Rainbow of Colors in the Sun," Simplemost, dated Jul. 17, 2019, pp. 1-9.

Sundicators, "Sundicators UV and Sunscreen Reminders," My Sun Protection, dated: Sep. 1, 2015, p. 1-3 <https://mysunprotection.com.au/collections/sundicators/UV-Indicators>.

Schneller.com, "Aircraft Laminates," Dated: Dec. 18, 2015, pp. 1-6 <https://web.archive.org/web/20151218030956/http://schneller.com/1-aircraft-laminates>.

Schneller.com, "AerFilm flex® Contour," Dated: Sep. 26, 2020, pp. 1-5 <https://web.archive.org/web/20200926124613/https://schneller.com/aircraft-decorative-laminates/aerfilm-flex-contour>.

Schneller.com, "AerFilm sofTouch," Date: Sep. 26, 2020, pp. 1-5 <https://web.archive.org/web/20200926125428/https://www.schneller.com/aircraft-decorative-laminates/aerfilm-softouch>.

Schneller.com, "AerFilm LHR®," Date: Jun. 26, 2016 , pp. 1-6 <https://web.archive.org/web/20160626072109/https://schneller.com/aircraft-decorative-laminates/aerfilm-lhr>.

Schneller.com, "AerFilm Flex®," Date Accessed: Jun. 26, 2016, pp. 1-5 <https://web.archive.org/web/20160626072436/https://schneller.com/aircraft-decorative-laminates/aerfilm-flex>.

Schneller.com, "AerTrim® LW," Date: Jun. 26, 2016, pp. 1-5 <https://web.archive.org/web/20160626115558/https://schneller.com/aircraft-decorative-laminates/aertrim-lw>.

Schneller.com, "AerTrim sofTouch®," Dated: Jun. 26, 2016, pp. 1-5 <https://web.archive.org/web/20160626132949/https://schneller.com/aircraft-decorative-laminates/aertrim-softouch>.

Schneller.com, "AerScreen™," Date: Jun. 26, 2016 pp. 1-4 <https://web.archive.org/web/20160626071006/https://schneller.com/aircraft-decorative-laminates/aerscreen>.

Schneller.com, "AerTrim® BD 100," Dated: Jun. 26, 2016, pp. 1-5 <https://web.archive.org/web/20160626113653/https://schneller.com/aircraft-decorative-laminates/aertrim-bd-100>.

Schneller.com, "AerLam™ LW," Date: Jun. 26, 2016, pp. 1-5 <https://web.archive.org/web/20160626131743/https://schneller.com/aircraft-decorative-laminates/aerlam-lw>.

Schneller.com, "AerShade®," Date: Jun. 26, 2016, pp. 1-4 <https://web.archive.org/web/20160626075415/https://schneller.com/aircraft-decorative-laminates/aershade>.

Schneller.com, "AerGlas™ I-V," Date: Jun. 26, 2016, pp. 1-5 <https://web.archive.org/web/20160626122844/https://schneller.com/aircraft-decorative-laminates/aerglas-i-v>.

Schneller.com, "AerTrim® LHR," Date: Jun. 26, 2016, pp. 1-5 <https://web.archive.org/web/20160626065554/https://schneller.com/aircraft-decorative-laminates/aertrim-lhr>.

Schneller.com, "Application Selector Tool," Date: Jan. 13, 2020, pp. 1-7 <https://web.archive.org/web/20200113080928/https://schneller.com/application-selector-tool>.

Schneller.com, "Indura GTGlas®," Date: Jun. 26, 2016, pp. 1-5 <https://web.archive.org/web/20160626131750/https://schneller.com/rail-decorative-thermoplastic-sheets/indura-gtglas>.

Schneller.com, "Indura GTFilm®," Date: Jun. 26, 2016, pp. 1-5 <https://web.archive.org/web/20160626132933/https://schneller.com/rail-interior-decorative-laminates/indura-gtfilm>.

Amazon.com, "DDSKY Ultraviolet Disinfection Lamp, DDSKY Effective UV Light Portable Germicidal Lamp Sanitizier USB Ultraviolet Bulb Sterilizer for Home Kitchen Bedroom Hospital," Dated Accessed: Jun. 15, 2020.

Amazon.com, "Padgene Ultraviolet UV Light Sanitizer Travel Wand, USB Portable Mini LED Sanitizer Disinfection Lamp for Household Office Travel Car Wardrobe Toilet 7W," Date Accessed: Jun. 15, 2020.

National Intellectual Property Administration, PRC, Notification of First Office Action for Application 201711222123X dated Jun. 24, 2022.

Extended European Search Report prepared by the European Patent Office in application No. EP 21 20 0593.8 dated Mar. 14, 2022.

Extended European Search Report prepared by the European Patent Office in application No. EP 21 19 8334.1 dated Mar. 2, 2022.

LCRHallcrest, Chameleon Photochromic Masterbatch, Specialist Colour Change Technology.

Colourchange a Division of LCR Hallcrest, Photochromic Plastic, https://www.colurchange.com/photochromic-plastic/#toggle-id-1.

European Patent Office, Extended European Search Report for Application 21199241.7-1012 / 4000648 dated Jun. 23, 2022.

European Patent Office, Communication Pursuant to Article 94(3) EPC for Application 21 198 334.1-1017 dated Sep. 9, 2023.

European Patent Office, Communication Pursuant to Article 94(3) EPC for Application 21 199 241.7-1012 dated Feb. 19, 2024.

* cited by examiner

SYSTEMS AND METHODS OF USE OF UV-RESPONSIVE LAMINATES AND METHODS OF FABRICATION THEREOF

CROSS-REFERENCE TO RELATED APPLICATION(S)

This application claims benefit of and priority to U.S. Provisional Application No. 63/121,476, filed Dec. 4, 2020, of which is hereby expressly incorporated by reference herein in its entirety.

FIELD

Aspects of the present disclosure relate to the ability to clean and confirm cleaning of surfaces using UV light.

BACKGROUND

Cleaning of surfaces involved in the delivery of a service to customers has become paramount in the current environment. In addition, confirming the cleanliness of surfaces correspondingly has similar importance. Current surface cleaning methods may not provide reliable indications that the cleaning process has been performed. Accordingly, neither the users of these surfaces nor those responsible for performing the cleaning processes may reliably confirm that the surfaces have been sufficiently cleaned. Accordingly, there remains a need for systems and methods to reliably clean and confirm that cleaning procedures have been executed.

SUMMARY

The present disclosure provides a laminate, in one aspect, the laminate including: a first layer having a photochromatic pigment, the photochromatic pigment being configured to change from a first state to a second state in response to exposure to an ultraviolet (UV) light source, the first state being invisible to a naked eye under ambient lighting and the second state being visible to the naked eye under ambient lighting; and a second layer, the second layer being a coupling layer configured to removably couple the laminate to a component.

In one aspect, in combination with any other laminate above or below, the laminate includes the first layer being formed from a polyvinyl material or a fiberglass material.

In one aspect, in combination with any other laminate above or below, the laminate includes the first layer being formed from a material that is at least 30% UV transparent within a predetermined wavelength.

In one aspect, in combination with any other laminate above or below, the laminate includes the material having a UV transparency of the predetermined wavelength from about 200 nanometers (nm) to about 360 nm.

In one aspect, in combination with any other laminate above or below, the laminate includes the material having a UV transparency of the he predetermined wavelength is from about 222 nm to about 254 nm.

In one aspect, in combination with any other laminate above or below, the laminate includes the first layer being formed from a material that is non-flammable.

In one aspect, in combination with any other laminate above or below, the laminate includes a plurality of edges defining a surface area of the laminate.

In one aspect, in combination with any other laminate above or below, the laminate includes the first layer having a plurality of indicators formed from the photochromatic pigment, the plurality of indicators being formed across less than an entirety of the surface area.

In one aspect, in combination with any other laminate above or below, the laminate includes the first layer having a plurality of indicators formed from the photochromatic pigment, the plurality of indicators being formed across an entirety of the surface area.

In one aspect, in combination with any other laminate above or below, the laminate includes the first layer having a plurality of indicators having at least one of a first color, a first material, or a first pattern that is different than at least one of a second color, a second material, or a second pattern of the first layer.

In one aspect, in combination with any other laminate above or below, the laminate includes the laminate being configured as a plurality of sections, each section of the plurality of sections being separated from an adjacent section of the plurality of sections by a series of perforations.

In one aspect, in combination with any other laminate above or below, the laminate includes the first layer having a plurality of indicators formed from the photochromatic pigment, the plurality of indicators being formed as an ordered array.

In one aspect, in combination with any other laminate above or below, the laminate includes the first layer further having a pigment texture including an embossed pattern, the photochromatic pigment being disposed in the embossed pattern.

In one aspect, in combination with any other laminate above or below, the laminate includes the second layer being formed from a polyvinyl material or a fiberglass material.

In one aspect, in combination with any other laminate above or below, the laminate includes the second layer having an adhesive.

In one aspect, in combination with any other laminate above or below, the laminate includes a backing layer removably coupled to the second layer.

In one aspect, in combination with any other laminate above or below, the second layer of the laminate does not include an adhesive.

In one aspect, in combination with any other laminate above or below, the laminate includes the photochromatic pigment having a first pigment and a second pigment, the first pigment being configured to change from the second state back to the first state after a first predetermined period of time, the second pigment being configured to change from the second state back to the first state after a second predetermined period of time, the first predetermined period of time being less than the second predetermined period of time.

In one aspect, in combination with any other laminate above or below, the laminate includes that the first layer is an outermost layer of the laminate.

In one aspect, in combination with any other laminate above or below, the laminate includes a protective layer formed on top of the first layer having the photochromatic pigment, the protective layer being an outermost layer of the laminate.

The present disclosure provides a method of forming a UV-responsive laminate, the method including disposing a photochromatic pigment on a laminate, the photochromatic pigment being configured to change from a first state to a second state in response to exposure to a UV light, the first state being invisible to a naked eye under ambient lighting and the second state being visible to the naked eye under ambient lighting, the laminate being formed from a polyvinyl material.

In one aspect, in combination with any other method of forming a UV-responsive laminate above or below, the method includes, prior to disposing of the photochromatic pigment, removably coupling the laminate to a component, the disposing of the photochromatic pigment being performed in-situ.

In one aspect, in combination with any other method of forming a UV-responsive laminate above or below, the method includes that the component is formed from a material selected from the group consisting of: a polymer, a metal, a composite material, an organic material, and combinations thereof.

In one aspect, in combination with any other method of forming a UV-responsive laminate above or below, the method includes disposing the photochromatic pigment to form an ordered array of photochromatic indicators.

The present disclosure provides a method of cleaning, the method including (a) exposing a laminate to an ultraviolet (UV) light source, the laminate being removably coupled to a component and including photochromatic pigment being configured in a first state, the first state being invisible to a naked eye under ambient lighting; (b) changing, by the photochromatic pigment, in response to absorbing UV light from the UV light source, from the first state to a second state, the second state being visible to the naked eye under ambient lighting, the second state indicating the laminate is clean; and (c) reverting, by the photochromatic pigment, after a predetermined period of time, from the second state to the first state.

In one aspect, in combination with any other method of cleaning above or below, the method includes (d) subsequent to (c), exposing the laminate to the UV light source to change the photochromatic pigment from the first state to the second state.

In one aspect, in combination with any other method of cleaning above or below, the method includes that the UV light source is configured to emit UV light within a wavelength range from about 200 nanometers (nm) to about 360 nm.

In one aspect, in combination with any other method of cleaning above or below, the method includes that the UV light source is configured to emit UV light within a wavelength range from about 222 nm to about 254 nm.

BRIEF DESCRIPTION OF THE DRAWINGS

So that the manner in which the above recited features can be understood in detail, a more particular description, briefly summarized above, may be had by reference to example aspects, some of which are illustrated in the appended drawings.

DETAILED DESCRIPTION

The present disclosure relates to the cleaning, e.g., the disinfection and sanitization of one or more surfaces of a component using non-contact cleaning. The non-contact cleaning may include as exposure to ultraviolet (UV) light. The cleaning discussed herein can, in some examples, include sterilization. As used herein, "sterilization" is a process that makes one or more surfaces of a component free from bacteria, viruses, fungi, or other living microorganisms. The surfaces discussed herein may be part of a public or private transportation vehicles (aerospace vehicles such as aircraft, spacecraft, marine vehicles, or the like, and non-aerospace transportation vehicles such as busses, cars, trains, boats, cruise ships), retail or food service locations, financial institutions, casinos, non-casino gaming environments (e.g., e-sports), or other locations, or other public or semi-public space having surfaces that can be contacted by multiple parties such that living microorganisms can be spread from the surface among and between parties that may or may not have contacted the surface. In some examples, UV light may be used alone, and in other examples, UV light may be used in combination with one or more cleaning agents, such as cleaning solvents, to remove contaminants such as dirt and oils as well as biologic elements such as viruses, fungi, mold, mildew, and bacteria such that the cleaned surfaces are not likely to transmit biologic contaminants among and between users of these surfaces.

In currently employed cleaning processes, a photo-luminescent element or elements can be used to indicate that rooms and surfaces, such as lavatories on aircrafts, have been cleaned. However, currently employed photo-luminescent processes may be commonly confirmed in a darkened passenger cabin, or other areas capable of having all light sources deactivated or otherwise covered, where photo-luminescent strips emit light from absorbed photons. Photo-luminescent inks currently used, may further be visible only while illuminated, and not by the naked eye under ambient light. In addition, some currently employed systems use photo-luminescent indicators that can be charged from a multitude of light sources such as ambient light sources in addition to cleaning sources such as UV lights. As such, the current photo-luminescent indicators might glow from being charged by these light sources, thereby undesirably providing a false reading of ultraviolet (UV) exposure and resultant clean status.

Using the systems and methods discussed herein, photochromatic pigments are used to indicate, to a party responsible for cleaning a surface as well as to a party who may use the surface, that the surface has been cleaned. The systems and methods discussed herein thus instill confidence and, in some examples, confirmation and auditability, that cleaning has been performed. The cleaning can be defined by a predetermined schedule set by a party who owns or rents the component(s), or by a local, state, or federal government regulation.

Photochromatic pigments may take various forms. As used herein, a "photochromatic indicator" is a printed text or graphic formed from one or more photochromatic pigments. Photochromatic indicators are one form which photochromatic pigments may take, wherein photochromatic pigment is disposed on a surface. A pigment such as a photochromatic pigment may also be used to form a "pigment texture." A "pigment texture," as discussed herein, is to mean a series of features including or a pattern of repeating features that are embossed or otherwise formed in a material such as a fiberglass, polyvinyl, textile, organic, or other material or combination of materials such that the features are formed to include a pigment such as a photochromatic pigment. Photochromatic pigments are configured to change from a first state to a second state for a predetermined period of time in response to absorbing UV light. A determination as to whether a photochromatic pigment is in a first state or a second state may be made by a naked eye under ambient light conditions. As discussed herein, a "first state" of a photochromatic pigment is to mean that the photochromatic pigment is invisible to the naked eye under ambient light. As discussed herein, a "second state" of a photochromatic pigment is to mean that the photochromatic pigment is visible to the naked eye under ambient light. The photochromatic pigments, when in a visible state, may be various colors such as red, orange, yellow, green, blue, purple, brown, black, or other colors or combinations of colors.

As used herein, "ambient light" is light present in a room from natural light (e.g., the sun), or existing room lighting, in contrast to lights used to illuminate particular aspects of or areas within room or another environment. As used herein, something that is "visible to the naked eye" can be seen without magnification, including something which is visible to a person or persons whom are wearing prescription glasses. The first states and the second states of photochromatic pigments and resultant indicators discussed herein can be confirmed by and are visible using the naked eye in ambient light, such that the environment including the photochromatic indicator may not be darkened in order to confirm cleaning. In other aspects of the present disclosure, the change from the first state to the second state can be additionally confirmed via an application on a mobile device or via a tactile change, for example, if a party who desires to confirm the change is vision-impaired or desires to create a record of the change using the mobile device. The ability to verify that a surface has been cleaned using the photochromatic indicators discussed herein provides assurance for the party cleaning the surface as well as for the party using the surface.

The first state of a photochromatic pigment, where the photochromatic pigment is invisible to the naked eye under ambient light, may indicate that the surface including the photochromatic pigment may not have been cleaned recently. In contrast, the second state of the photochromatic pigment, where the photochromatic pigment is visible to the naked eye under ambient light, indicates that the surface including the photochromatic pigment has been cleaned. For example, photochromatic pigments may change from a first state that is invisible to the naked eye under ambient light, to a second state that is visible to the naked eye under ambient light upon the absorption of certain UV light. The photochromatic pigments can be in the forms of liquid, solid (e.g., powder), colloids (e.g., slurry), or other forms or combinations of forms. Depending upon the example, the photochromatic pigments can be used in indicators as liquid or gel reservoirs, paints or other coatings, and applied via various printing methods either at an original equipment manufacturer of, for example, a laminate that is to be installed in an aircraft or other vehicle or environment, or in-situ. As used herein, "in-situ" use of photochromatic pigments is to mean the application of photochromatic pigment by one or more means to a surface, such as a laminate surface, that is already installed in an aircraft, vehicle, or other environment, in contrast to forming the laminate at an OEM to include the photochromatic pigment. As used herein, the terms "paint" and "coating" may be used interchangeably to mean various types of materials (such as photochromatic indicators) applied in one or more layers to one or more surfaces via various application means. The laminates discussed herein as including photochromatic pigment can be referred to as "UV-responsive laminates" but may also be referred to as "laminates."

The photochromatic pigments discussed herein are disposed on laminates that are removably coupled to components which are installed in environments including aircraft. As used herein, a laminate can be "removably coupled" to one or more components such that the uncoupling of the laminate and the component does not damage the component and such that a second laminate may be subsequently applied to the component. In some examples, the component may be cleaned when the laminate is removed, prior to removably coupling a new laminate to the component. Accordingly, the photochromatic pigments are reversible so that the surfaces can be cleaned in a plurality of iterations while the component is installed in the environment without the laminate being replaced. The ability to repeatedly clean the surface, e.g., the laminate, without removing the laminate enables efficient maintenance and cleaning of these environments. As used herein, "reversible" is to mean that UV light is applied to the photochromatic indicator to change it from a first state to a second state. In this example, after a predetermined period of time that may range from about 10 minutes to about 24 hours, the photochromatic indicator changes from the second state back to the first state. In other examples, the predetermined period of time can be from about 30 minutes to about 3 hours. In still other examples, the predetermined period of time of the first state can be from about 2 hours to about 6 hours. As used herein, "about" is to mean within +/−5% of a stated target value, maximum, or minimum value.

Example Laminate Structures

Figure 1A:
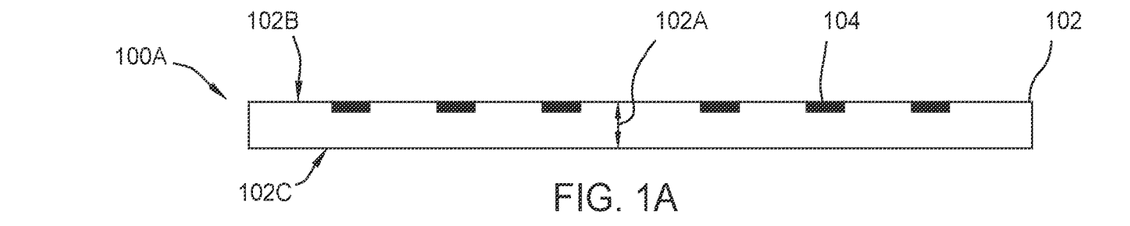
FIGS. 1A-1D depict examples of laminates according to aspects of the present disclosure.

FIGS. 1A-1D depict examples of laminates according to aspects of the present disclosure. FIG. 1A illustrates a cross-section of a first laminate 100A having a first layer 102. The first layer 102 has a thickness 102A and includes a first side 102B and a second side 102C. The second side 102C is configured to be able to be removably coupled to a component (not shown) which may be formed from a material including a metal, polymer, composite, or from a combination of materials. The removably coupling of the first laminate 100A to a component may be via a chemical adhesive, a pressure-based adhesive, a heat-activated adhesive, and a thermoset adhesive, or other adhesives or combinations of adhesives as appropriate. In one example, the thickness 102A of the first layer 102 may be from about 0.25 mils (1 mil=0.0001 inches (in.)) 10.0 mils. In another example, the thickness 102A of the first layer 102 may be from about 0.50 mils to about 7.0 mils. In still another example, the thickness 102A of the first layer 102 may be from about 0.75 mils to about 5.0 mils.

The first side 102B of the first layer 102 of the first laminate 100A includes a plurality of photochromatic pigment 104. The plurality of photochromatic pigment 104 can take various forms, as discussed at least in FIGS. 2A-2C below. The plurality of photochromatic pigment 104 may be formed on the first side 102B of the first layer 102 via various printing methods, such as silk-screen printing, digital printing, ink jet printing, or another printing process capable of depositing the plurality of photochromatic pigment 104. The first layer 102 can be formed from one or more materials, including a polyvinyl material or a fiberglass material. In one example, the first layer 102 can be formed from a polyvinyl fluoride film (PVF) or a fiberglass reinforced emboss resin. In some examples, the first layer 102 includes two or more types of material that may be layered vertically along the y-axis, horizontally along the x-axis, or otherwise configured (an example coordinate system is included adjacent to FIG. 1A).

Figure 1B:
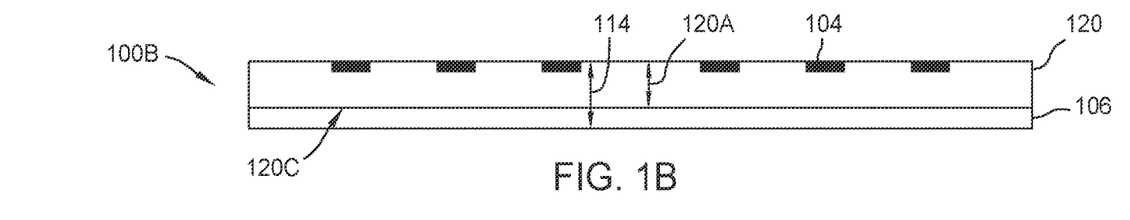

FIG. 1B depicts a second laminate 100B having a first layer 120 that may be similar in composition to the first layer 102 of FIG. 1A and includes a photochromatic pigment 104 which can be arranged in various configurations as discussed below in FIGS. 2A-2C. In contrast to the first laminate 100A in FIG. 1A, the second laminate 100B includes a first side 120B and a second side 120C, and an adhesive layer 106 formed on the second side 102C. The adhesive layer 106 may include a chemical adhesive, a pressure-activated adhesive, a thermoplastic adhesive, a heat-activated adhesive, or combinations thereof. The adhesive layer 106 is configured to removably couple the second laminate 100B to a component (not shown). In some examples, an adhesive can be deposited on the component as well, such that the adhesive of the component is selected to bond to the adhesive layer 106. In one example, the adhesive layer 106 is formed over the entire surface area (discussed below in FIG. 2A) of the second side 120C of the first layer 120. In another example, the adhesive layer 106 is formed over one or more portions of the second side 120C which are less than the entire surface area of the second side 120C. The configuration of the second laminate 100B may be used, for example, when a roll of laminate is formed at an OEM. In this example, the second laminate 100B may be cut to form a portion of the second laminate 100B to couple the portion to a component. The coupling of any laminate or portion of laminate discussed herein may be referred to herein as "installation." In another example, the roll of the second laminate 100B could include a plurality of perforations defining a plurality of pre-formed laminates. The plurality of pre-formed laminates may include the same shape and dimensions, or may vary in a single roll in shape, dimensions, or both.

The second laminate 100B has a thickness 114. In one example, the thickness 114 of the second laminate 100B may be from about 0.25 mils (1 mil=0.0001 inches (in.)) 10.0 mils. In another example, the thickness 114 of the second laminate 100B may be from about 0.50 mils to about 7.0 mils. In still another example, the thickness 114 of the second laminate 100B may be from about 0.75 mils to about 5.0 mils. The first layer 120 may have a thickness 120A that may be, in one example, from about 1% to about 50% of the thickness 114 of the second laminate 100B. The first layer 120 may have a thickness 120A that may be, in another example, from about 3% to about 30% of the thickness 114 of the second laminate 100B. In still another example, the first layer 120 may have a thickness 120A that may be from about 5% to about 10% of the thickness 114 of the second laminate 100B.

Figure 1C:
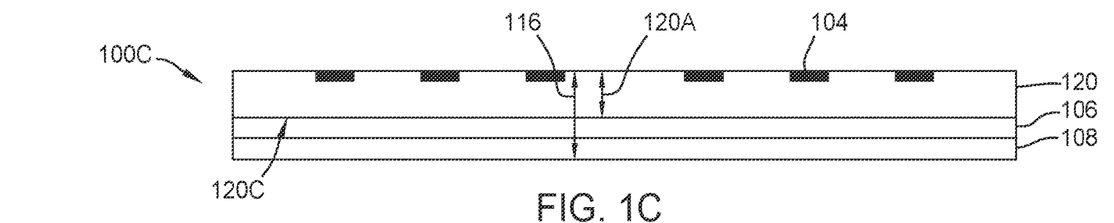

FIG. 1C depicts a third laminate 100C having a first layer 120 and an adhesive layer formed on the second side 120C of the adhesive layer 106, similar to those layers as discussed above in FIG. 1B. In contrast to FIG. 1B, the third laminate includes a backing layer 108 formed on the adhesive layer 106. The backing layer 108 can include an organic material (paper), textile (woven material), or other material. The backing layer 108 is configured to be removed from the adhesive layer 106 prior to the third laminate 100C being removably coupled to a component (not pictured). The configuration of the third laminate 100C may be used, for example, when a roll of laminate is formed at an OEM. In this example, the roll could include a plurality of perforations (not shown here) defining a plurality of pre-formed laminates. The plurality of pre-formed laminates may include the same shape and dimensions, or may vary in a single roll in shape, dimensions, or both. In other examples, the configuration of the third laminate 100C may be as one or more unconnected pieces that may have various shapes configured to couple to components of aircrafts, ships (including cruise ships), other transportation vehicles or other components located in retail or restaurant environments.

The third laminate 100C has a thickness 116. In one example, the thickness 116 of the third laminate 100C may be from about 0.25 mils (1 mil=0.0001 inches (in.)) 10.0 mils. In another example, the thickness 116 of the third laminate 100C may be from about 0.50 mils to about 7.0 mils. In still another example, the thickness 116 of the third laminate 100C may be from about 0.75 mils to about 5.0 mils. The first layer 120 may have a thickness 120A that may be, in one example, from about 1% to about 50% the thickness 116 of the third laminate 100C. The first layer 120 may have a thickness 120A that may be, in another example, from about 3% to about 30% of the thickness 116 of the third laminate 100C. In still another example, the first layer 120 may have a thickness 120A that may be from about 5% to about 10% of the thickness 116 of the third laminate 100C.

Figure 1D:
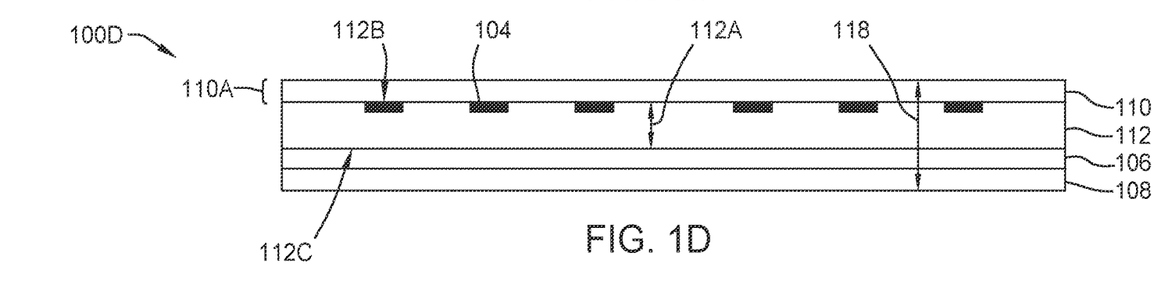

FIG. 1D depicts a fourth laminate 100D. The fourth laminate 100D includes a first layer 110 formed on a first side 112B of a second layer 112 that may also be referred to as the photochromatic pigment layer. In some examples, the first layer 110 can be formed from a polyvinyl material or a fiberglass material. In one example, the first layer 110 can be formed from a polyvinyl fluoride film (PVF) or a fiberglass reinforced emboss resin. The first layer 110 can have a thickness 110A. In one example, the thickness 110A may be from about 0.25 mils to about 10 mils. In another example, the thickness 110A of the first layer 110 may be from about 5% to about 33% of the thickness 118 of the fourth laminate 100D. In contrast to the first layer 102 discussed in FIGS. 1A-1C, the first layer 110 of the fourth laminate 100D does not include a photochromatic pigment. Rather, the first layer 110 is a protective layer formed over the second layer 112 which includes the photochromatic pigment 104. Similarly to third laminate 100C, the fourth laminate 100D includes an adhesive layer 106 formed on a second side 112C of the second layer 112, and a backing layer 108 coupled to the adhesive layer 106.

The fourth laminate 100D has a thickness 118. In one example, the thickness 118 of the fourth laminate 100D may be from about 0.25 mils to about 10.0 mils. In another example the thickness 118 of the fourth laminate 100D may be from about 0.50 mils to about 7.0 mils. In still another example, the thickness 118 of the fourth laminate 100D may be from about 0.75 mils to about 5.0 mils. The first layer 110 may have a thickness 110A that may be, in one example, from about 1% to about 50% the thickness 118 of the fourth laminate 100D. The first layer 11 may have a thickness 110A that may be, in another example, from about 3% to about 30% of the thickness 118 of the fourth laminate 100D. In still another example, the first layer 110 may have a thickness 110A that may be from about 5% to about 10% of the thickness 118 of the fourth laminate 100D. The second layer 112 has a thickness 112A. In one aspect, the thickness 112A of the second layer 112 may be from about 1% to about 50% the thickness 118 of the fourth laminate 100D. In another aspect, the thickness 112A of the second layer 112 may be from about 3% to about 30% of the thickness 118 of the fourth laminate 100D. In still another aspect, the thickness 112A of the second layer 112 may be from about 5% to about 10% of the thickness 118 of the fourth laminate 100D. In one example, the thickness 110A is less than the thickness 112A. In one aspect, a ratio of the thickness 110A to the thickness 112A may be from about 1:1 to about 1:10. In another aspect, the ratio of the thickness 110A to the thickness 112A may be from about 1:2 to about 1:8. In still another aspect, the ratio of the thickness 110A to the thickness 112A may be from about 1:3 to about 1:6.

The laminates discussed herein, including the laminates discussed above and below, include one or more layers fabricated from non-flammable material. "Non-flammable" material(s), as discussed herein, are materials that may melt or otherwise degrade in response to heat and/or flames but that do not ignite nor release toxic fumes. Materials from which the laminates discussed herein are formed may be selected based upon state, local, or federal regulations applicable to the environments in which the laminates are installed (e.g., aircraft, food service, cruise ships/boats, military vehicles, automobiles, trains, etc.).

Figure 2A:
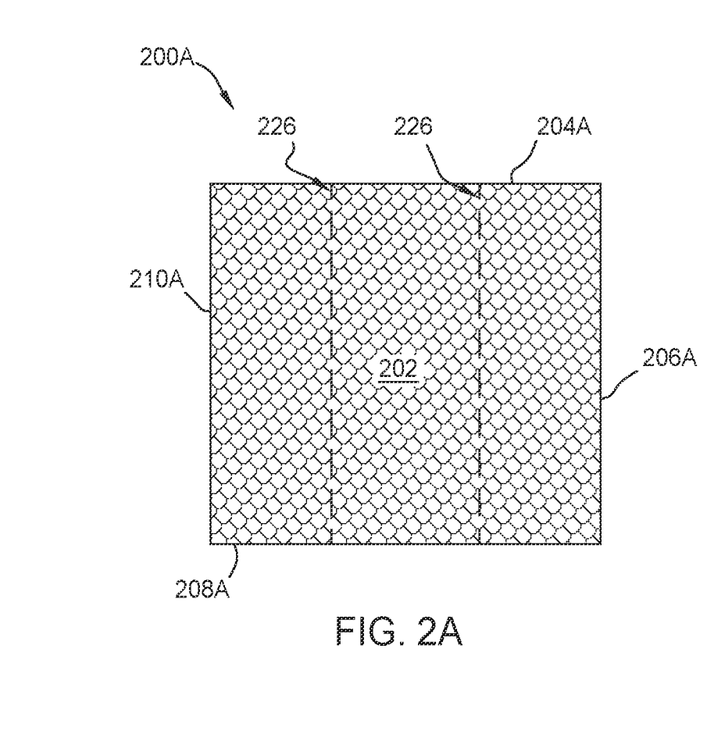
FIGS. 2A-2E depict examples of laminates including photochromatic pigment according to aspects of the present disclosure.
Figure 2B:
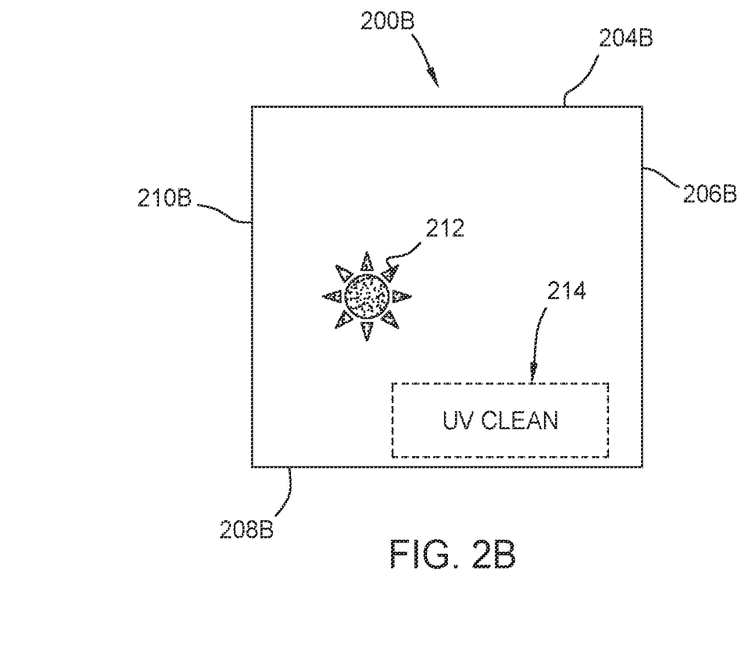
Figure 2C:
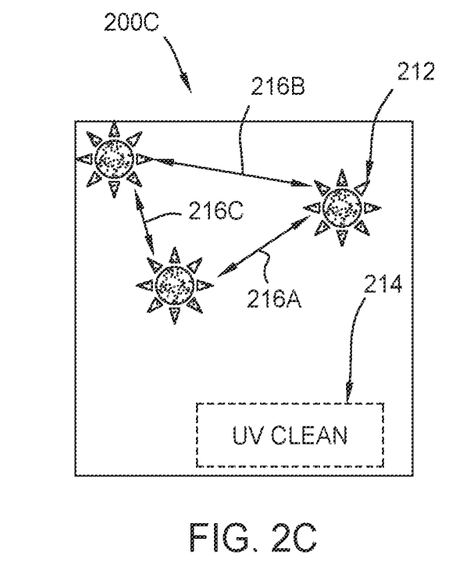

FIGS. 2A-2C depict examples of laminates including photochromatic pigment according to aspects of the present disclosure. The laminates illustrated in FIGS. 2A-2E may be formed in various manner and from various materials, such as the materials discussed above in FIGS. 1A-1D.

FIG. 2A illustrates a first laminate 200A having a pigment texture 202 formed from photochromatic pigment. A pigment texture can include one or more colors of pigment (including but not limited to photochromatic pigment) that can be arranged in various patterns and configurations. In one example, a first pigment included in a pigment texture can include a photochromatic pigment and a non-photochromatic pigment, such that the non-photochromatic pigment can be visible under ambient light with the naked eye and the photochromatic pigment in a first state is invisible to the naked eye under ambient light and a second state which, after the photochromatic pigment is exposed to UV light, is visible to the naked eye under ambient light. In this example, the photochromatic pigment reverts back to the first state from the second state after a predetermined reversion time. As discussed herein, a "reversion time" is a time that it takes a photochromatic pigment to change from a second state (visible to the naked eye under ambient light) back to the first state (invisible to the naked eye under ambient light). Depending upon the example, the reversion time of a photochromatic pigment can be from about 2 minutes to about 6 hours or more. In one example, a gradient of pigment that includes two or more colors of pigment can be used to form the pigment texture. In one example, the gradient includes a photochromatic pigment and a non-photochromatic pigment, as discussed above. In another example, the gradient of pigments can include two or more photochromatic pigments of varying colors, each having a different predetermined reversion time.

The first laminate 200A has a polygonal shape defined by a first side 204A, a second side 206A, a third side 208A, and a fourth side 210A. The first side 204A, the second side 206A, the third side 208A, and the fourth side 210A define a surface area of the first laminate 200A In other examples, the first laminate 200A may take other shapes or combinations of shapes as appropriate for installation in various environments having varying geometries. In one example, the pigment texture 202 can extend across a portion of the first laminate 200A that is less than an entire surface area of the first laminate 200A. In other examples, the pigment texture 202 may be formed on the first laminate 200A on portion of the surface area of the first laminate 200A that is less than its entire surface area. The first laminate 200A further includes pluralities of perforations 226, which can be used to separate the first laminate 200A into sections which can be applied to one or more components or one or more regions of the same components.

FIG. 2B illustrates a second laminate 200B having at least one deposition of photochromatic pigment and does not include a pigment texture. The second laminate 200B has a polygonal shape defined by a first side 204B, a second side 206B, a third side 208B, and a fourth side 210B. The first side 204B, the second side 206B, the third side 208B, and the fourth side 210B define a surface area of the second laminate 200B. In other examples, the second laminate 200B may take other shapes or combinations of shapes as appropriate for installation in various environments having varying geometries. The at least one deposition of photochromatic pigment in the example of the second laminate 200B may include a graphic indicator 212 or a text indicator 214. In the example in FIG. 2B, a single graphic indicator 212, a single text indicator 214, or a combination of the two may be formed on the entire surface area of the second laminate 200B. This is in contrast to the partial views of laminates in FIGS. 2C-2E which may include various ordered or random arrangements of photochromatic indicators.

Figure 2D:
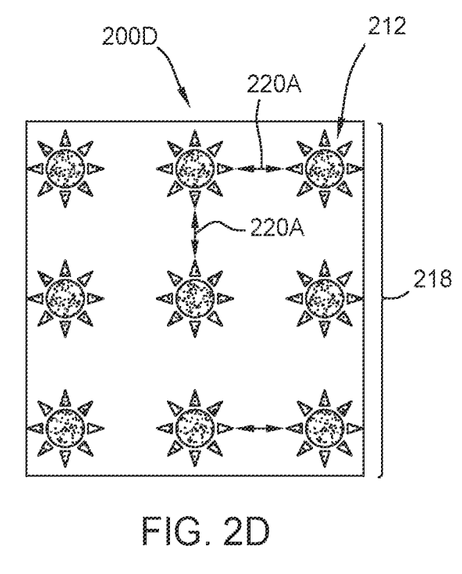
Figure 2E:
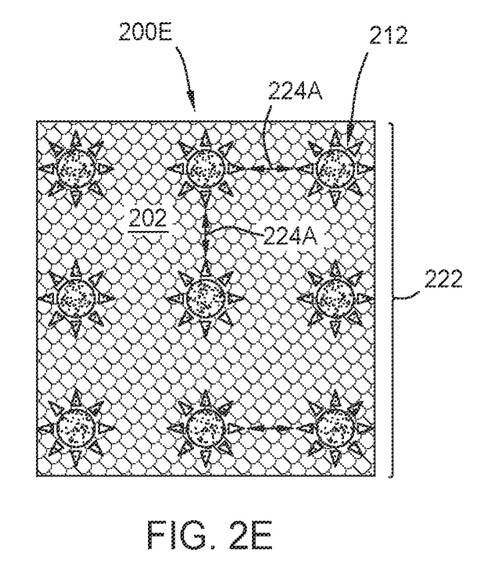

In contrast to FIGS. 2A and 2B, which show entire laminates FIGS. 2C-2E each depict partial top-views of laminates according to aspects of the present disclosure. FIG. 2C depicts a third laminate 200C that includes a plurality of randomly arranged graphic indicators 212. A "random array" may mean that the distances (216A, 216B, 216C) between each pair of adjacent graphic indicators 212 are different. In some examples, the plurality of graphic indicators 212 shown in FIG. 2C are the only photochromatic indicators on the third laminate 200C. In other examples, other pluralities of graphic indicators 212 having non-uniform spacing (in contrast to the ordered arrays discussed below) may be included in the third laminate 200C. In other examples, which can be combined with various examples herein, the third laminate 200C can include one or more text indicators 214 which may be arranged in various patterns.

FIG. 2D depicts a fourth laminate 200D that includes an ordered array 218 of photochromatic indicators, shown here as graphic indicators 212. In other examples, text indicators may also be formed as an ordered array. As discussed herein, an "ordered array" includes a plurality of photochromatic pigment depositions of a graphic, text, or combination, where each deposition of photochromatic pigment is positioned equidistance from each adjacent deposition. The ordered arrays discussed herein may extend over an entire surface area of a laminate or over a portion of the surface area of a laminate that is less than the entire surface area. In the example in FIG. 2D, the fourth laminate 200D includes an ordered array 218 of graphic indicators 212, each of which is spaced equidistant 220A from one or more adjacent graphic indicators 212. As discussed above, the graphic indicators 212 can take various shapes including acting as brand identifiers. In other examples, the ordered array 218 may include text indicators or combinations of graphic indicators and text indicators. While graphic indicators 212 having the same shape and dimensions are illustrated herein, in other examples, graphic indicators having various sizes and/or shapes may be used to form the ordered array 218.

FIG. 2E depicts a fifth laminate 200E that combines the pigment texture 202 shown in FIG. 2A and the ordered array 222 that may be similar to the ordered array 218 shown in FIG. 2D. As discussed herein with respect to the ordered array 218 in FIG. 2D, the fourth laminate 200D includes graphic indicators 212 in the ordered array 222, each of which is spaced equidistant 224A from one or more adjacent graphic indicators 212. As discussed above, the graphic indicators 212 can take various shapes including acting as brand identifiers. In other examples, the ordered array 218 may include text indicators or combinations of graphic indicators and text indicators. While graphic indicators 212 having the same shape and dimensions are illustrated herein, in other examples, graphic indicators having various sizes and/or shapes may be used to form the ordered array 222.

Example Environments Including UV-Responsive Laminates

Figure 3:
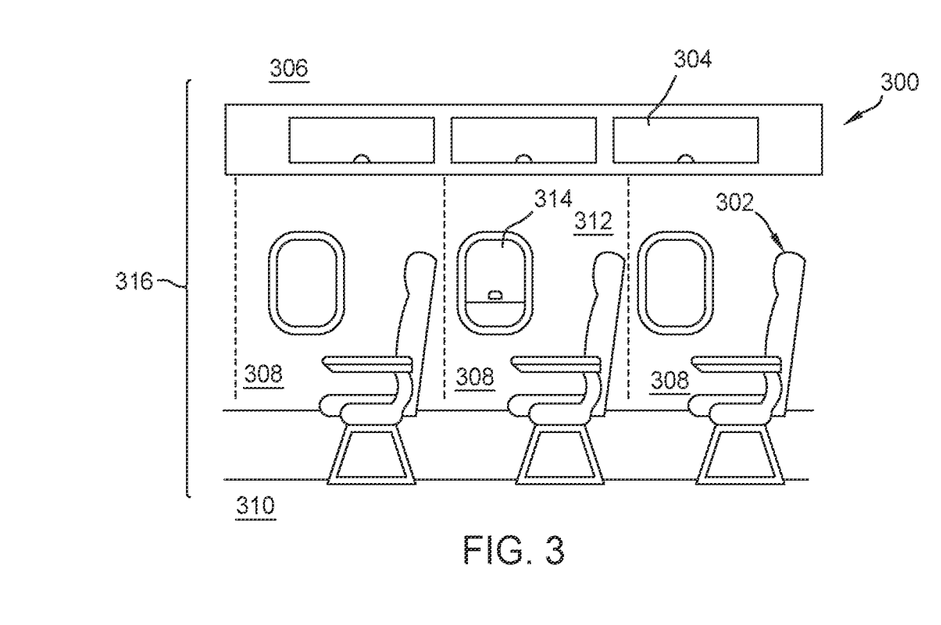
FIG. 3 depicts an illustrative cabin interior of an aircraft that may include one or more UV-responsive laminates ("laminates") according to aspects of the present disclosure.

FIG. 3 depicts an illustrative cabin interior 316 of an aircraft 300 that may include one or more UV-responsive laminates ("laminates") according to aspects of the present disclosure. The cabin interior 316 may include structural components covered with one or more examples of a laminate as disclosed herein, such as a laminate 304. The structural components include a cabin interior sidewall 306 and panels 308. The structural components are shown herein as having a laminate coupled thereto, and may further include floor panels 310, stowage bins 312, and window elements 314 (e.g., window masks, window reveals, window shades and the like). Further in this example, elements of seating 302 may include laminates (e.g., seat console, seat interior, seat panel, seat backs, seat shell, tray table, and the like). Other structural components of the aircraft 316 not shown here that may have UV-responsive laminates removably coupled thereto include: insulation barriers, moisture barriers, composite noise panels, lavatory and galley panels and structures, bulkheads, partitions, ceilings, door linings, entryways, and cargo bin liners. The laminates in FIG. 3 are shown having the photochromatic pigment in a first state, where the photochromatic pigment is not visible to the naked eye under ambient light.

Figure 4:
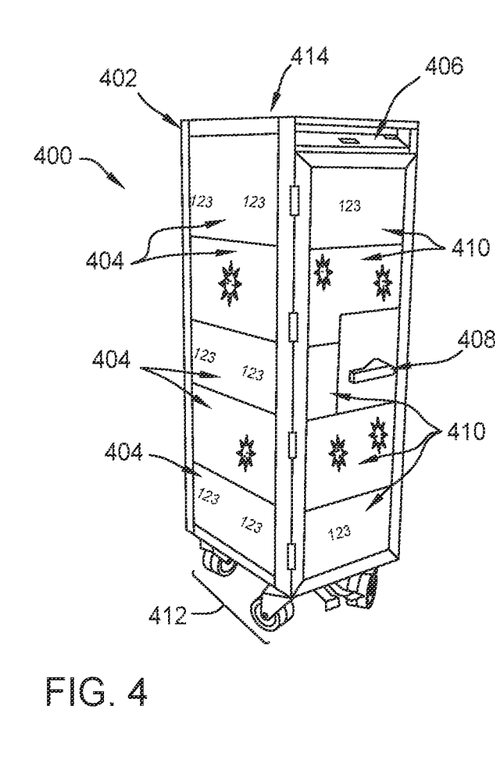
FIG. 4 depicts an illustrative service cart that may be used in aircrafts and may include one or more laminates including photochromatic pigment according to aspects of the present disclosure.

FIG. 4 depicts an illustrative service cart 400 that may be used in aircrafts and may include one or more laminates including photochromatic pigment according to aspects of the present disclosure. The service cart 400 can include laminates, shown herein as being removably coupled to a plurality of side panels 404 and a plurality of front panels 410. It is understood that there is a second plurality of side panels located on another side of the service cart 400 that is parallel and opposite to the side shown in FIG. 4 as having the plurality of side panels 404 which further includes side panels having laminates coupled thereto. The service cart 400 further includes one or more trays 406 that may be slidingly engaged with the service cart 400, such that the trays 406 can be pulled out from the service cart 400 to act as serving surfaces, in some examples without being fully disengaged from the service cart 400. In this example, the one or more trays 406 can have laminates having photochromatic pigment as discussed herein removably coupled thereto. The plurality of front panels 410 having laminates including photochromatic pigment removably coupled thereto may include panels associated with drawers, bins, or other storage apparatuses. The service cart 400 can further include a frame 402 that may be formed from aluminum or other materials, and a handle 408 that may be configured to position the service cart 400, and/or may be configured to provide access to a compartment of the service cart 400. In some examples, the frame 402 has laminates including photochromatic pigment removably coupled thereto. The service cart 400 additionally includes a plurality of movable elements 412 configured to transport the service cart 400 among and between various locations on an aircraft as well off of the aircraft (e.g., for service cart 400 maintenance). In one example, the movable elements 412 include wheels. The service cart 400 further includes a top surface 414 that may have a laminate coupled thereto.

The UV-responsive laminates discussed in FIG. 4 can include photochromatic pigments in the form of one or more pigment textures. In other examples, the laminates can include photochromatic indicators such as "UV clean," brand identifiers (shown herein as "123") associated with the airline, aircraft manufacturer, food service provider, other advertisers, or combinations thereof. The service cart 400 is an example service cart that may, in other examples, may include different geometries, dimensions, and configurations of drawers, shelves, refrigeration/warming devices, or materials. For example purposes, the laminates of FIG. 4 that are removably coupled to the plurality of side panels 404 and the plurality of front panels 410 are shown in a second state, indicating that the service cart 400 has been cleaned, such that the photochromatic pigment is visible to the naked eye under ambient light.

Figure 5:
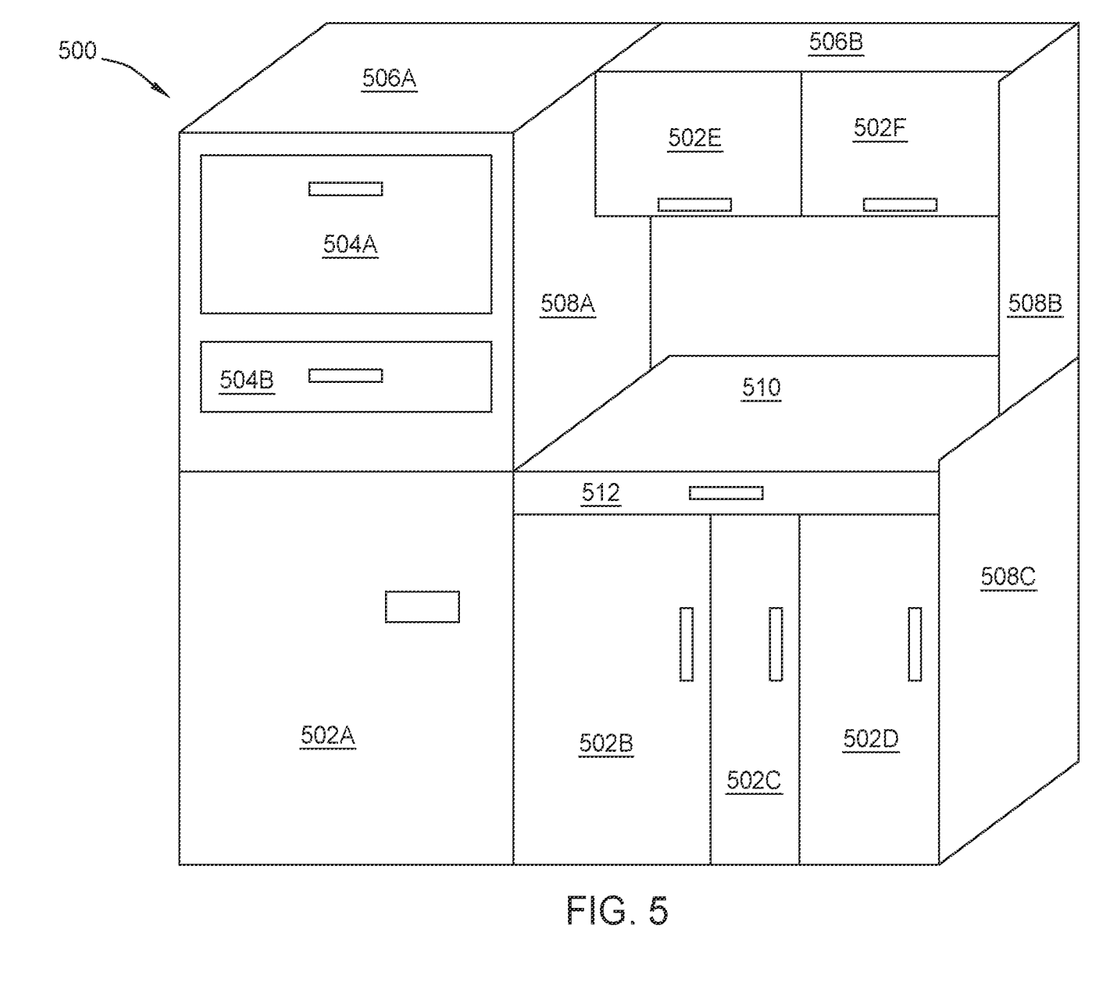
FIG. 5 depicts an example galley that can include UV-responsive laminates as discussed herein removably coupled to various surfaces.

FIG. 5 depicts an example galley 500 that can include UV-responsive laminates as discussed herein removably coupled to various surfaces. The galley 500 may be included in an aircraft, sea vessel, bus, train, restaurant, food kiosk, or other location where food preparation may occur. The galley 500 can have the laminates coupled to storage cabinets (502C, 502D, 502E, and 502F) used for non-perishable food or serving/cooking supplies, one or more trash or recycling bins 502B, and/or one or more drawers 512. The galley 500 may further include the UV-responsive laminates coupled to refrigerated storage 502A and warming apparatuses 504A, 504B, as well as a servicing surface 510. The laminates may be further removably coupled to structural elements and surfaces such as the top surfaces 506A, 506B, and the side surfaces 508A, 508B, 508C.

The UV-responsive laminates discussed in FIG. 5 can include photochromatic pigments in the form of one or more pigment textures. In other examples, the laminates can include photochromatic indicators such as "UV clean," brand identifiers for the airline, aircraft manufacturer, food service provider, other advertisers, or combinations thereof. The galley 500 is an example service cart that may, in other examples, may include different configurations of storage apparatuses (drawers, cabinets, etc., heating and cooling devices, serving surfaces and devices, or structural elements and surfaces. The galley 500 may be cleaned in between flights when passengers are not on board. In other examples, the galley 500 may be cleaned in whole or in part during flight when the passenger cabin includes passengers. The cleaning of the galley 500 can be visually confirmed using the naked eye under ambient light via the photochromatic pigment included in the laminates discussed above. One or more aspects of the galley 500 may be cleaned in flight, for example, before or after snack or meal service, or if contacted by crew or passengers. For example purposes, the laminates of FIG. 5 are shown in a first state where the photochromatic pigment is invisible to the naked eye.

Example Cleaning System

Figure 6:
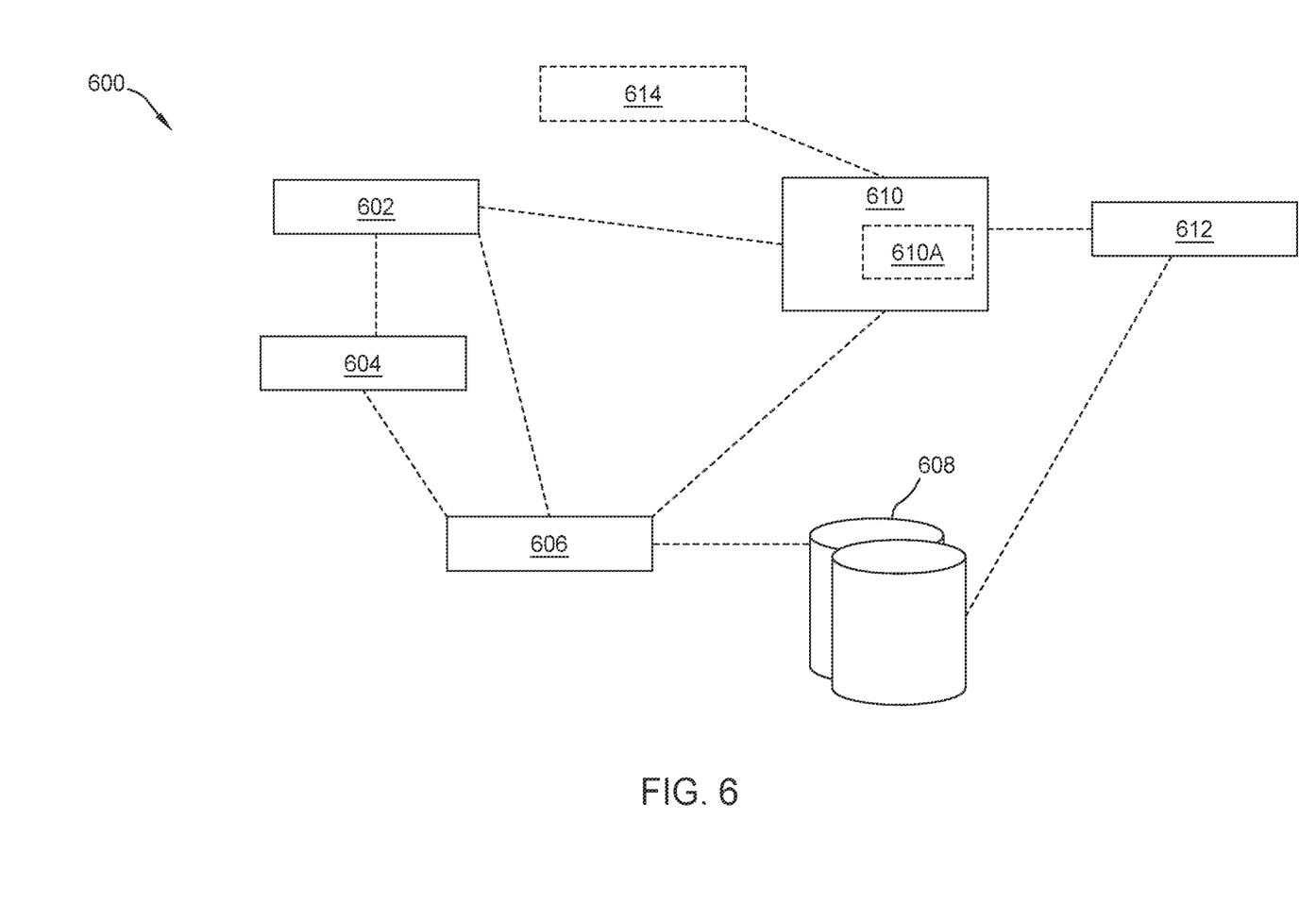
FIG. 6 depicts an example cleaning system according to aspects of the present disclosure.

FIG. 6 depicts an example cleaning system 600 according to aspects of the present disclosure. The cleaning system 600 includes a UV light source 602 that may include or be configured to couple to a power source 604. The UV light source 602 can be configured as a stand-alone, wireless device that includes the power source 604 which may be a rechargeable battery. As discussed in detail below, the UV light source 602 can be configured to emit wavelengths from about 100 nanometers (nm) to about 400 nm. Also, the wavelength can be from about 200 nm to about 360 nm. In another example, the predetermined wavelength range is from about 200 nm to about 230 nm. In still another example, the predetermined wavelength range is from about 235 nm to about 280 nm. In yet another example, the predetermined wavelength range is from about 315 nm to about 400 nm. Moreover, in some examples, the UV light source can be configured to emit wavelengths from about 222 nm to about 254 nm. In some examples, the UV light source 602 can have an elongated geometry referred to as a "wand," a circular geometry, polygonal geometry, or can have a combination of two or more geometries. The UV light discussed herein can be UVA, UVB, UVC, or combinations of UV light types. The UV light source 602 can include a plurality of LED lights. In other examples, the UV light source 602 can be configured as a wired device that may or may not be connected to the power source 604 when in use. In still other examples, the UV light source 602 can be configured as a self-driven or manually-driven device or collection of devices that can be coupled to a ceiling of an area to be cleaned and/or a floor of an area to be cleaned. In other examples, the UV light source 602 can be included in a robotically or manually-driven cleaning device that may or may not include the power source 604. In one example, the UV light source 602 is included in a device that can be programmed to move along a predetermined path to clean a plurality of surfaces.

The UV light source 602 can be configured to operate at a wavelength or within a range such that the one or more photochromatic pigments 610A included in or formed on a laminate 610 change from a first state to a second state in response to absorbing the energy from the UV light source 602. Depending upon the example, the one or more photochromatic pigments 610A can be reversible as discussed above. In some examples, the laminate 610, which may be configured with photochromatic pigment 610A, for example, as shown in FIGS. 1A-1D, FIGS. 2A-2C, or combinations thereof. Accordingly, the photochromatic pigment 610A may be formed as a pigment texture or as one or more photochromatic indicators. In one example, the photochromatic pigment 610A can be configured to include two or more types (colors) of photochromatic pigment or two or more concentrations of the same type (color) of photochromatic pigments such that the laminate 610 has a color gradient which forms over time in one or more directions as the photochromatic pigment 610A changes from the second state back to the first state. In one example, the color gradient could be configured to indicate to a cleaner or cleaning system sensor when the photochromatic pigment 610A is changing from the first state to the second state.

The photochromatic pigment 610A and laminate 610 can each be formed from one or more materials configured to be used and approved for use (e.g., by one or more government authorities and/or by an OEM or customer's internal regulations) in one or more of an aircraft, automobile, hospital, restaurant, retail location, hotel/resort, or other locations as discussed herein. In some locations, each of the photochromatic pigment 610A and laminate 610 will thus be formed from one or more materials configured to resist humidity, fire, wide pH ranges, heat, cold, or other conditions without detaching or uncoupling from an associated component. In some examples, each of the photochromatic pigment 610A and laminate 610 is formed from a material chosen to prevent the release of toxic fumes during a fire.

In some examples, as discussed herein, the laminate 610 includes the photochromatic pigment 610A prior to being installed in, for example, an aircraft. In other examples, the photochromatic pigment 610A is added to the laminate 610 in-situ, subsequent to installation. In this example, an in-situ printing device 614 may be employed to dispose the photochromatic pigment 610A on the laminate 610 without uninstalling the laminate 610. That is, the photochromatic pigment 610A may be applied to the laminate 610 in-situ, within the environment in which the laminate 610 is installed. In still other examples, the laminate 610 may include the photochromatic pigment 610A from either the OEM process or a subsequent in-situ process using the in-situ printing device 614, but additional photochromatic pigment 610A may be added subsequent to installation.

In some examples, the cleaning system 600 includes a server computer 606 having a non-transitory memory configured to store a plurality of logic in the form of cleaning programs, cleaning schedules, and cleaning records. This information and other information may be stored on one or more data stores 608 which may be part of a cloud computing system. The UV light source 602 and the power source 604 may be in communication with and/or controlled by the server computer 606. In some examples, a mobile device 612 such as a phone, tablet, personal data assistant, laptop computer, or wearable smart device can include an app configured to determine when the photochromatic pigment 610A is in the first state or the second state. In other examples, the mobile device 612 may be in communication with and able to control the UV light source 602 and the power source 604. The cleaning system 600 may be used to clean laminates according to various methods discussed herein.

Example Method of Cleaning System Use

Figure 7:
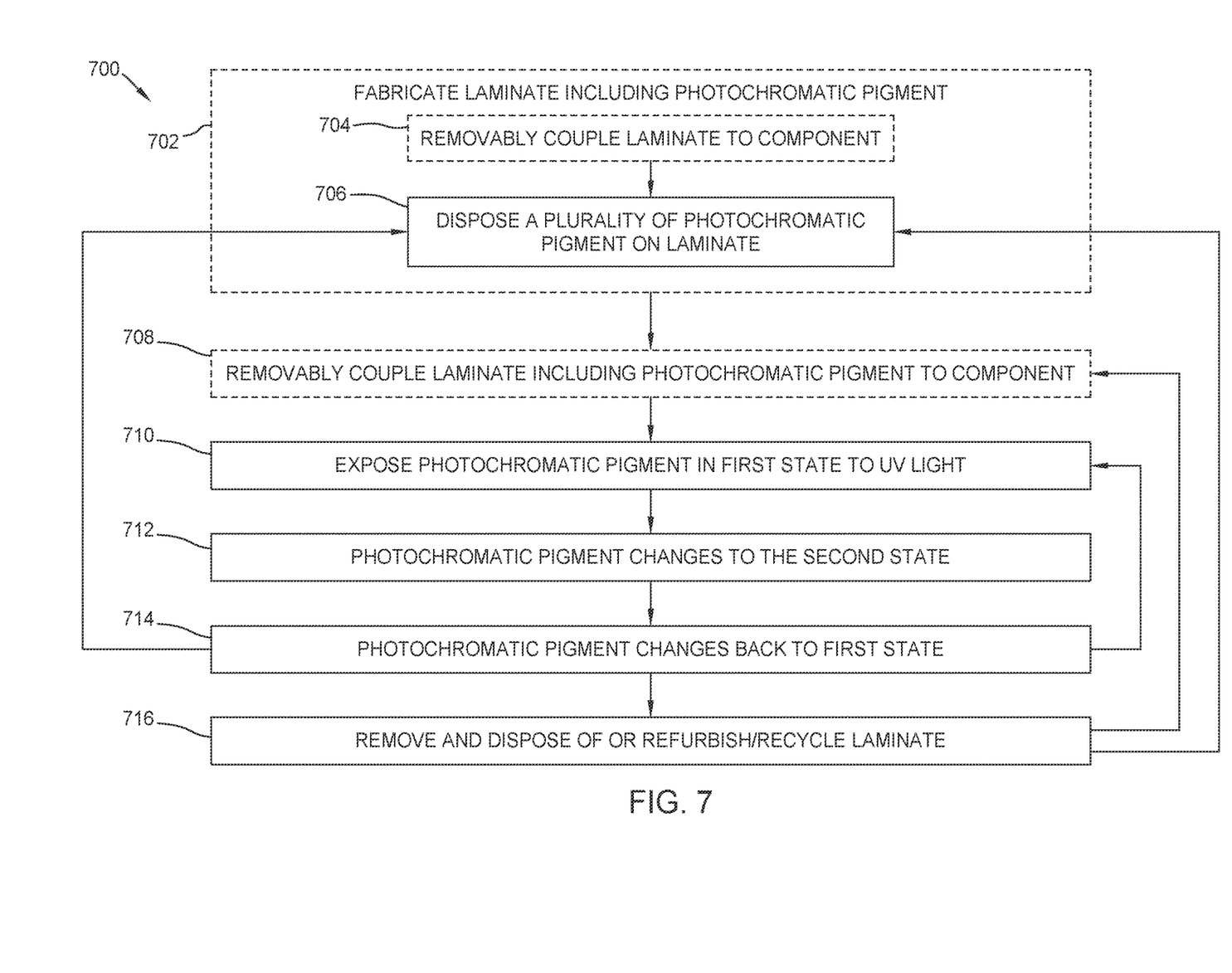
FIG. 7 depicts a flow chart of a method of using cleaning systems including laminates according to aspects of the present disclosure.

FIG. 7 depicts a flow chart of a method 700 of using cleaning systems to clean laminates according to aspects of the present disclosure. At operation 702, a laminate including photochromatic pigment is fabricated (702—Fabricate laminate including photochromatic pigment). In one example, operation 702 includes disposing a plurality of photochromatic pigment on a laminate at operation 706 (706—Dispose a plurality of photochromatic pigment on laminate). In one example, operation 706 may be performed on a laminate that has not been installed. In another example, prior to operation 706, the laminate is installed, that is, the laminate is removably coupled to a component, at optional operation 704 (704—Removably couple laminate to component).

Depending upon the example, the laminate installed at operation 704 may or may not include photochromatic pigment. The photochromatic pigment disposed at operation 706 may be disposed on the laminate as a pigment texture, one or more photochromatic indicators, or combinations thereof. The photochromatic pigment may be disposed at operation 706 in the first state, where it is invisible to the naked eye under ambient light. In other examples, the photochromatic pigment may be disposed at operation 706 in the second state, where it is visible to the naked eye under ambient light, for example, by disposing the photochromatic pigment under UV light. This may be done, for example, to ensure the placement and formation of the pigment texture and/or photochromatic indicators. In this example, the photochromatic pigment may revert to the first state from the second state prior to installation as discussed below. The photochromatic pigment may be disposed at operation 706 as a single photochromatic indicator, an ordered array of photochromatic indicators, or in other forms or patterns. The photochromatic pigment disposed at operation 706 can be configured to change from a first state to a second state in response to exposure to a UV light. The first state of the photochromatic pigment is invisible to a naked eye under ambient lighting and the second state is visible to the naked eye under ambient lighting. As discussed herein, the surface upon which the photochromatic pigment is disposed, whether in-situ after operation 704 or at an OEM prior to installation, may be formed from a polyvinyl material. In other examples, the surface upon which the photochromatic pigment is disposed may be formed from other materials that may be selected, for example, to meet OEM, customer, government, or other rules or regulations associated with durability, safety (e.g., flammability), or other aspects of an environment in which the laminates are installed. The component which the laminate is removably coupled to may be formed from a material such as a polymer, a metal, a composite material, an organic material, and combinations thereof.

At optional operation 708, if the laminate has not been previously installed at operation 704, the laminate including the photochromatic pigment is removably coupled to a component (installed) (708—Removably couple laminate including photochromatic pigment to component). At operation 710, the laminate having photochromatic pigment configured in the first state is exposed to UV light (710—Expose photochromatic pigment in first state to UV light).

In one example, the UV light source is configured to emit UV light within a wavelength range at operation 710 from about 200 nanometers (nm) to about 360 nm. In another example, the UV light source is configured to emit UV light within a wavelength range at operation 710 from about 220 nanometers (nm) to about 300 nm. In yet another example, the UV light source is configured to emit UV light within a wavelength range at operation 710 from about 222 nm to about 254 nm.

At operation 712, in response to exposure to the photochromatic pigment at operation 710, the photochromatic pigment changes to the second state, causing it to be visible to the naked eye in ambient light (712—Photochromatic pigment changes to the second state). The changing of the photochromatic pigment from the first state to the second state at operation 712 may occur instantaneously, that is, the change to the second state at operation 712 may be visible to the naked eye under ambient light upon exposure to the UV light, in about less than 0.5 second. In other examples, the change at operation 712 from the first state to the second state may occur during a period from about 0.1 seconds to about 10 seconds. In still other examples, the change at operation 712 from the first state to the second state may occur during a period from about 0.3 second to about 7 seconds. In other examples, the change at operation 712 from the first state to the second state may occur during a period from about 0.5 seconds to about 5 seconds.

Subsequently, after a predetermined period of time, at operation 714, the photochromatic pigment changes (reverts) back to the first state from the second state, indicating that the laminate including the photochromatic pigment is clean (714—Photochromatic pigment changes back to the first state). In one example, the photochromatic pigment may remain in the second state, subsequent to operation 712 but before operation 714, being visible to the naked eye under ambient light, for a predetermined time period from about 5 seconds to about 60 minutes. In one example, the photochromatic pigment may remain in the second state, subsequent to operation 712 but before operation 714, being visible to the naked eye under ambient light, for a predetermined time period from about 5 seconds to about 180 minutes. In another example, the photochromatic pigment may remain in the second state, subsequent to operation 712 but before operation 714, being visible to the naked eye under ambient light, for a predetermined time period from about 30 seconds to about 60 minutes. In yet another example, the photochromatic pigment may remain in the second state, subsequent to operation 712 but before operation 714, being visible to the naked eye under ambient light, for a predetermined time period from about 60 seconds to about 15 minutes.

In some examples, subsequent to operation 714, the method 700 returns to operation 710 for one or more iterations, such that the laminate including the photochromatic pigment is cleaned for a plurality of iterations without being removed or refurbished. In some examples, if the photochromatic pigment included in the laminate has broken down or is otherwise no longer changing to the second state at operation 712 in response to UV light exposure at operation 710, the laminate can be removed (uninstalled) from the component at operation 716 and may be disposed of or refurbished or recycled (716—Remove and dispose of or refurbish/recycle laminate). In other examples, if the photochromatic pigment included in the laminate has broken down or is otherwise no longer changing to the second state at operation 712 in response to UV light exposure at operation 710, the method 700 may return to operation 706 where another plurality of photochromatic pigment may be disposed on the laminate, either in-situ after operation 714 or after removal subsequent to operation 716. This in-situ disposal of photochromatic pigment at operation 706 may also occur, for example, if a different type of photochromatic pigment is desired on the laminate (e.g., a new brand identifier or other text or symbol). In some examples, subsequent to removing the laminate at operation 716, the method 700 proceeds to operation 708 (or operation 704) and a new, different laminate is removably coupled to the component.

Using the systems and methods discussed herein, various surfaces having UV-responsive laminates coupled thereto can be verifiably cleaned by the transition of the photochromatic pigments included in the laminates changing from the first state to the second state. This visual confirmation can lead to more efficient cleaning processes as well as improved safety for both the parties cleaning the surfaces as well as the parties using the environments in which the laminates are installed. The photochromatic pigment can be customized to include various colors or combinations of colors, including gradients, as well as brand identifiers. The UV-responsive laminates can have the photochromatic pigment included therein at the OEM when the laminates are formed. The laminates may also have the photochromatic pigment disposed thereon or re-applied in-situ, after the laminate has already been removably coupled to a surface of a component. The UV-responsive laminates can be configured to removably couple to a variety of types of surfaces that are formed from a wide variety of materials and located in various types of environments, providing a reliable method of safely cleaning a wide breadth of environments, from aircrafts and other transportation vehicles to retail, gaming, and food service locations.

In the current disclosure, reference is made to various aspects. However, it should be understood that the present disclosure is not limited to specific described aspects. Instead, any combination of the above features and elements, whether related to different aspects or not, is contemplated to implement and practice the teachings provided herein. Additionally, when elements of the aspects are described in the form of "at least one of A and B," it will be understood that aspects including element A exclusively, including element B exclusively, and including element A and B are each contemplated. Furthermore, although some aspects may achieve advantages over other possible solutions and/or over the prior art, whether or not a particular advantage is achieved by a given aspect is not limiting of the present disclosure. Thus, the aspects, features, aspects and advantages disclosed herein are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

As will be appreciated by one skilled in the art, aspects described herein may be embodied as a system, method or computer program product. Accordingly, aspects may take the form of an entirely hardware aspect, an entirely software aspect (including firmware, resident software, micro-code, etc.) or an aspect combining software and hardware aspects that may all generally be referred to herein as a "circuit," "module" or "system." Furthermore, aspects described herein may take the form of a computer program product embodied in one or more computer readable storage medium(s) having computer readable program code embodied thereon.

Program code embodied on a computer readable storage medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations and/or block diagrams of methods, apparatuses (systems), and computer program products according to aspects of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block(s) of the flowchart illustrations and/or block diagrams.

These computer program instructions may also be stored in a computer readable medium that can direct a computer, other programmable data processing apparatus, or other device to function in a particular manner, such that the instructions stored in the computer readable medium produce an article of manufacture including instructions which implement the function/act specified in the block(s) of the flowchart illustrations and/or block diagrams.

The computer program instructions may also be loaded onto a computer, other programmable data processing apparatus, or other device to cause a series of operational steps to be performed on the computer, other programmable apparatus or other device to produce a computer implemented process such that the instructions which execute on the computer, other programmable data processing apparatus, or other device provide processes for implementing the functions/acts specified in the block(s) of the flowchart illustrations and/or block diagrams.

The flowchart illustrations and block diagrams in the Figures illustrate the architecture, functionality, and operation of possible implementations of systems, methods, and computer program products according to various aspects of the present disclosure. In this regard, each block in the flowchart illustrations or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order or out of order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

While the foregoing is directed to aspects of the present disclosure, other and further aspects of the disclosure may be devised without departing from the basic scope thereof, and the scope thereof is determined by the claims that follow.

What is claimed is:

1. A method of cleaning, comprising:
   (a) exposing a laminate having a first layer to an ultraviolet (UV) light source, the laminate being removably coupled to a component, wherein a photochromatic pigment is disposed on the laminate and configured in a first state, wherein the first layer is formed from a polyvinyl material or fiberglass material;
   (b) changing, by the photochromatic pigment, in response to absorbing UV light from the UV light source, from the first state to a second state, the second state indicating the laminate is clean; and
   (c) reverting, by the photochromatic pigment, after a predetermined period of time, from the second state to the first state,
   wherein the photochromatic pigment comprises:
      a first pigment that changes from the second state back to the first state after a first predetermined period of time; and a second pigment that changes from the second state back to the first state after a second predetermined period of time that is longer than the first predetermined period of time.

2. The method of claim 1, further comprising (d) subsequent to (c), exposing the laminate to the UV light source to change the photochromatic pigment from the first state to the second state.

3. The method of claim 1, wherein the UV light source is configured to emit UV light within a wavelength range from about 200 nanometers (nm) to about 360 nm.

4. The method of claim 1, wherein the UV light source is configured to emit UV light within a wavelength range from about 222 nm to about 254 nm.

5. The method of claim 1, wherein the polyvinyl material or the fiberglass material is UV transparent.

6. The method of claim 1, wherein the polyvinyl material comprises a polyvinyl fluoride film.

7. The method of claim 1, wherein the fiberglass material comprises a fiberglass reinforced emboss resin.

8. The method of claim 1, wherein the laminate comprises a second layer formed from a polyvinyl material or a fiberglass material.

9. The method of claim 1, wherein the UV light source is configured to emit UV light within a wavelength range from about 200 nanometers (nm) to about 360 nm, the first layer is formed from the polyvinyl material, and the polyvinyl material comprises a polyvinyl fluoride film.

10. The method of claim 1, wherein the UV light source is configured to emit UV light within a wavelength range from about 200 nanometers (nm) to about 360 nm, the first layer is formed from the fiberglass material, and the fiberglass material comprises a fiberglass reinforced emboss resin.

11. The method of claim 8, wherein the second layer includes an adhesive.

12. The method of claim 8, wherein the second layer does not include an adhesive.

13. The method of claim 8, wherein the first layer has a first thickness from about 0.25 mil to about 10 mil.

14. The method of claim 8, wherein the second layer has a second thickness from about 0.25 mil to about 10 mil.

15. The method of claim 8, wherein the polyvinyl material comprises a polyvinyl fluoride film.

16. The method of claim 8, wherein the fiberglass material comprises a fiberglass reinforced emboss resin.

17. The method of claim 8, wherein the first layer and the second layer have a thickness ratio of about 1:1 to about 1:10.

18. The method of claim 11, further comprising a backing layer removably coupled to the second layer.

19. The method of claim 17, wherein the first layer and the second layer have a thickness ratio of about 1:2 to about 1:8.

20. The method of claim 19, wherein the first layer and the second layer have a thickness ratio of about 1:3 to about 1:6.

* * * * *